(12) United States Patent
Gill et al.

(10) Patent No.: US 9,700,587 B2
(45) Date of Patent: Jul. 11, 2017

(54) DELIVERY OF A THERAPEUTIC AGENT TO THE CEREBRAL CORTEX BY ADMINISTERING A VIRAL VECTOR BY CONVECTION ENHANCED DIFFUSION INTO THE WHITE MATTER OF THE BRAIN

(71) Applicant: RENISHAW PLC, Gloucestershire (GB)

(72) Inventors: Steven Streatfield Gill, Bristol (GB); Neil Barua, Bristol (GB)

(73) Assignee: RENISHAW PLC, Wotton-under-Edge (GB)

( * ) Notice: Subject to any disclaimer, the term of this patent is extended or adjusted under 35 U.S.C. 154(b) by 0 days.

(21) Appl. No.: 14/891,891

(22) PCT Filed: May 16, 2014

(86) PCT No.: PCT/GB2014/051509
§ 371 (c)(1),
(2) Date: Nov. 17, 2015

(87) PCT Pub. No.: WO2014/184576
PCT Pub. Date: Nov. 20, 2014

(65) Prior Publication Data
US 2016/0143966 A1  May 26, 2016

(30) Foreign Application Priority Data

May 17, 2013 (GB) .................................. 1308917.2

(51) Int. Cl.
*A61K 48/00* (2006.01)
*C12N 15/86* (2006.01)
*C12N 15/63* (2006.01)
*A61K 35/761* (2015.01)
*A61K 9/00* (2006.01)
*A61M 25/00* (2006.01)
*C12N 7/00* (2006.01)
*A01K 67/00* (2006.01)

(52) U.S. Cl.
CPC .......... *A61K 35/761* (2013.01); *A61K 9/0085* (2013.01); *A61K 48/0075* (2013.01); *A61K 48/0083* (2013.01); *A61M 25/0021* (2013.01); *C12N 7/00* (2013.01); *C12N 15/86* (2013.01); *A61M 2025/0042* (2013.01); *C12N 2710/10041* (2013.01); *C12N 2750/14343* (2013.01); *C12N 2799/025* (2013.01); *C12N 2799/04* (2013.01)

(58) Field of Classification Search
CPC .............. A61K 35/761; A61K 48/0075; A61K 48/0083; A61K 9/0085; C12N 15/86; C12N 2750/14343; C12N 2799/025; C12N 2799/04; C12N 2710/10041
USPC .............................. 424/93.2; 435/456, 320.1
See application file for complete search history.

(56) References Cited

U.S. PATENT DOCUMENTS

| 5,720,720 A * | 2/1998 | Laske | A61M 25/0075 604/21 |
| 8,901,077 B2 * | 12/2014 | White | A61K 48/0008 514/15.2 |
| 2004/0076613 A1 * | 4/2004 | Mazarakis | A61K 38/1866 424/93.2 |
| 2005/0010261 A1 * | 1/2005 | Luders | A61N 1/36082 607/45 |
| 2011/0212055 A1 * | 9/2011 | Commissiong | A61K 35/30 424/85.2 |
| 2012/0027726 A1 * | 2/2012 | Bankiewicz | A61K 48/0075 424/93.2 |
| 2012/0209110 A1 * | 8/2012 | Bankiewicz | A61B 5/055 600/431 |

FOREIGN PATENT DOCUMENTS

| EP | 1262188 A1 | 12/2002 |
| WO | 0207774 A2 | 1/2002 |
| WO | 0236829 A2 | 5/2002 |
| WO | 03004660 A1 | 1/2003 |
| WO | 03007785 A2 | 1/2003 |
| WO | 03/077785 A1 | 9/2003 |
| WO | 2004091718 A1 | 10/2004 |
| WO | 2006119341 A2 | 11/2006 |
| WO | 2008/062173 A1 | 5/2008 |
| WO | 2010071454 A1 | 6/2010 |
| WO | 2010088560 A1 | 8/2010 |
| WO | 2011098769 A1 | 8/2011 |
| WO | 2012098367 A1 | 7/2012 |
| WO | 2012159052 A2 | 11/2012 |

OTHER PUBLICATIONS

Bienemann et al., "The development of an implantable catheter system for chronic or intermittent convection-enhanced delivery," Journal of Neuroscience Methods, 2012; 203:284-91.
Bobo et al., "Convection-enhanced delivery of macromolecules in the brain," Proc Natl Acad Sci U S A, 1994; 91:2076-80.
Prange et al., "Defining brain mechanical properties: effects of region, direction, and species," Stapp Car Crash Journal, 2000; 44:205-13.
White et al., "A robust MRI-compatible system to facilitate highly accurate stereotactic administration of therapeutic agents to targets within the brain of a large animal model" Journal of neuroscience methods, 2011; 195:78-87.
Hadaczek et al., "Transduction of Nonhuman Primate Brain with Adeno-Associated Virus Serotype 1: Vector Trafficking and Immune Response", Human Gene Therapy, vol. 20, No. 3, Mar. 1, 2009, pp. 225-237, ISSN: 1043-0342.

(Continued)

*Primary Examiner* — Quang Nguyen
(74) *Attorney, Agent, or Firm* — Oliff PLC (57) ABSTRACT

Methods for delivering a therapeutic agent to a cerebral cortex or to the cerebral cortex and spinal cord include administering a viral vector that includes the therapeutic agent into white matter of a brain in order to deliver the therapeutic agent to the cerebral cortex or to the cerebral cortex and spinal cord. Kits for performing such methods may include at least one viral vector, at least one therapeutic agent, and a convection enhanced delivery (CED) catheter.

14 Claims, 6 Drawing Sheets

(56) References Cited

OTHER PUBLICATIONS

White et al., "An evaluation of site-specific immune responses directed against first-generation adenoviral vectors administered by convection-enhanced delivery", The Journal of Gene Medicine, vol. 13, No. 5, May 1, 2011, pp. 269-282, ISSN: 1099-498X.
Barua et al., "Convection-enhanced delivery of AAV2 in white matter—A novel method for gene delivery to cerebral cortex", Journal of Neuroscience Methods, vol. 220, No. 1, Aug. 27, 2013, pp. 1-8.

* cited by examiner

DELIVERY OF A THERAPEUTIC AGENT TO THE CEREBRAL CORTEX BY ADMINISTERING A VIRAL VECTOR BY CONVECTION ENHANCED DIFFUSION INTO THE WHITE MATTER OF THE BRAIN

FIELD OF INVENTION

The present invention relates to viral vectors for use in the treatment of neurological disorders wherein the viral vectors are being administered into the white matter of the brain in order to deliver therapeutic agents to the cerebral cortex or to the cerebral cortex and spinal cord and methods of delivering therapeutic agents to the cerebral cortex or to the cerebral cortex and spinal cord comprising administering viral vectors into white matter of the brain.

BACKGROUND TO THE INVENTION

Convection-enhanced delivery (CED) describes a method of direct drug delivery to the brain though intraparenchymal microcatheters along an infusion-mediated pressure gradient. The technique allows drugs which do not cross the blood-brain barrier to be delivered in therapeutic concentrations throughout large volumes of brain tissue, whilst minimizing systemic exposure.

Since Bobo et al.'s original description of pressure-mediated infusion of macromolecules in white matter (Bobo et al., 1994), CED of therapeutic agents has been applied to a wide range of neurological disorders in both experimental studies and clinical trials. The majority of clinical studies have focused on disorders in which the pathology is localised to either white matter, or to deep gray matter structures such as malignant glioma and Parkinson's Disease. Direct delivery of therapeutics to the cerebral cortex, however, remains challenging.

Targeting therapeutic agents to the cerebral cortex could be beneficial in a number of neurological diseases, most notably Alzheimer's disease and other forms of dementia, amyotrophic lateral sclerosis, multiple sclerosis and stroke. Convection-enhanced delivery of adeno-associated virus (AAV)-based vectors to the thalamus has previously been shown to result in transgene expression in widespread cortical areas as a consequence of both anterograde and retrograde axonal transport of AAV vectors. However, selective targeting of agents to limited areas of cortex would require convection-enhanced delivery to specific thalamic nuclei which are not easily identified with conventional imaging methods. Additionally, due to the location of the thalamus deep within the brain surgical targeting to this area can be difficult and associated with increased risks of complications such as haemorrhage.

Intrathecal delivery of therapeutic agents is known for spinal anaesthesia, chemotherapy and pain management. However, this delivery route is associated with a large number of side effects such as nausea and dizziness and is therefore not suitable for more widespread application.

It is an object of the present invention to provide a new delivery route for therapeutic agents into the central nervous system (CNS), particularly into the cerebral cortex and spinal cord.

SUMMARY OF THE INVENTION

In a first aspect the invention provides a method for delivering a therapeutic agent into the cerebral cortex or cerebral cortex and spinal cord comprising administering a viral vector comprising the therapeutic agent into white matter of the brain.

In a second aspect the invention provides a viral vector for use in the treatment of neurological disorders wherein the viral vector comprises a therapeutic agent and is administered into the white matter of the brain in order to deliver the therapeutic agent to the cerebral cortex or to the cerebral cortex and spinal cord. Administration of the viral vector into the white matter of the brain as described herein includes administration wherein the viral vector is being administered and is to be administered into the white matter of the brain.

In a further aspect the invention provides a kit for use in the treatment of neurological disorders comprising at least one viral vector and at least one therapeutic agent.

DESCRIPTION

The present invention allows a viral vector to be administered into the brain to target the cerebral cortex or cerebral cortex and spinal cord. In more detail, the viral vector is administered into white matter of the brain and from there can be delivered to white or gray matter of the brain and to the spinal cord, in particular to the anterior horn and anterior horn cells of the spinal cord. In preferred embodiments of the invention the viral vector comprises a therapeutic agent, such as a transgene.

Preferably the method comprises administering a viral vector into white matter of the brain. More preferably, the viral vector is administered below a targeted cortical region at a junction of cortical gray matter and underlying white matter. In other words, in preferred embodiments of the invention the viral vector is to be administered into subcortical white matter ventral or inferior to a targeted cortical region. Suitable cortical regions include the motor cortex, the visual cortex and the auditory cortex. Administering the viral vector into the white matter below a targeted cortical region leads to axonal transport of the vector into overlying areas of the cortex and/or into the spinal cord. The present invention therefore provides a method for delivering a therapeutic agent to a specific region of the cerebral cortex by administering a viral vector to an underlying region of white matter. Furthermore, without being bound by hypothesis, it is believed that infusion of viral vectors below a targeted cortical region at a junction of cortical gray matter and underlying white matter gains access to cerebral cortex layer 5, which has the largest spread with the CNS and enables transport of the therapeutic agents through the spinal cord. Axonal transport of the viral vector or product of transgene expression to the spinal cord allows the vector or product of transgene expression to reach the anterior or posterior horn of the spinal cord. In particular it allows the vector or product of transgene expression to reach the anterior or posterior horn cells of the spinal cord.

The present invention additionally provides a viral vector for use in the treatment of neurological disorders wherein the viral vector is administered into the white matter of the brain in order to deliver a therapeutic agent to the cerebral cortex or to the cerebral cortex and spinal cord. The viral vector is administered into the white matter of the brain of a subject, the subject preferably being a mammal, more preferably a primate, especially a human.

In preferred embodiments of the invention the viral vector is administered by convention enhanced delivery (CED). Convection enhanced delivery is well known in the art. It means the delivery of a pharmaceutical, or other composition, to the brain under a positive pressure gradient via a narrow catheter, usually having an inner diameter of less than 500 µm, more usually less than 250 µm. Administration of the pharmaceutical or other composition by CED leads to a greater volume of distribution than is typically achieved by intracerebral injection or infusion.

The viral vector is preferably for administration via at least one convection enhanced delivery catheter, especially an intraparenchymal catheter. More preferably it is for delivery via at least two, at least three or four or more such catheters. In embodiments of the invention the viral vector is to be administered by at least one, preferably at least two convention enhanced delivery catheters. One or more catheters may be chronically implanted into a patient allowing repeat infusions of the chemotherapy agent.

Suitable viral vectors for use in the invention include all serotypes of Adeno Associated Virus (AAV) (including but not limited to AAV2, AAV5 and AAV6), Herpes simplex virus, Baculovirus, Rabies Virus and Human Immunodeficiency Virus (HIV). Preferably the viral vector is AAV5, AAV2 or a hybrid comprising genomic and/or capsid materials from more than one serotype such as AAV2/5.

The viral vector may be administered at a concentration of from $10^5$ to $10^{15}$ Vg/ml, preferably from $10^8$ to $10^{13}$ Vg/ml. In preferred embodiments of the invention the viral vector is administered at a concentration of about $10^{10}$ Vg/ml.

Generally, 1 ml to 500 ml of viral vector may be infused, preferably 50 ml to 300 ml may be infused, more preferably 50 ml to 150 ml may be infused. In embodiments of the invention about 100 ml of viral vector may be infused.

The viral vector is preferably for infusion at a flow rate of 0.5 µl/min to 20 µl/min, preferably 1 µl/min to 10 µl/min, more preferably 2.5 µl/min to 5 µl/min.

The viral vector is preferably for administration by infusion for between 4 and 24 hours, especially for at least 5, 6, 7, 8, 9, 10, 11, 12, 13, 14, 15 or 16 hours and/or for less than 23, 22, 21, 20, 19, 18, 17, 16, 15, 14, 13, 12, 11, 10, 9 or 8 hours. It is preferably for infusion for around 8 hours. In embodiments of the invention the viral vector is for infusion over a period of up to 72 hours, preferably up to 48 hours.

Whether or not the viral vector is for administration for a number of consecutive days or for regular administration over a number of days, it may independently or additionally be for administration weekly, fortnightly, monthly, every six, eight, twelve or fifteen or more weeks. For example, a cycle of two or three days of infusions may be repeated every three months. Alternatively, it may be for administration in a series of cycles of infusions, with 6, 7, 8, 9, 10, 11 or 12 months between the end of a first cycle of infusions and the next cycle of infusions.

The viral vector may be administered in combination with artificial cerebrospinal fluid (aCSF). ACSF as used in the present invention may comprise glucose, proteins and ionic constituents. Preferably the aCSF comprises NaCl at a similar concentration to that found in natural CSF, that is to say the concentration is preferably within 15%, more preferably within 10% of the concentration in natural CSF. Preferably the aCSF comprises NaHCO$_3$ at a similar concentration to that found in natural CSF, that is to say the concentration is preferably within 15%, more preferably within 10% of the concentration in natural CSF. Preferably the aCSF comprises KCl at a similar concentration to that found in natural CSF, that is to say the concentration is preferably within 10%, more preferably within 10% of the concentration in natural CSF. Preferably the aCSF comprises NaH$_2$PO$_4$ at a similar concentration to that found in natural CSF, that is to say the concentration is preferably within 15%, more preferably within 10% of the concentration in natural CSF. Preferably the aCSF comprises MgCl$_2$ at a similar concentration to that found in natural CSF, that is to say the concentration is preferably within 15%, more preferably within 10% of the concentration in natural CSF. The aCSF can comprise glucose at a similar concentration to that found in natural CSF, that is to say the concentration is within 15%, preferably within 10% of the concentration in natural CSF. In preferred embodiments of the invention, the aCSF may omit glucose, so as to reduce the likelihood of bacterial growth in any catheter used to administer the composition to a subject. Most preferably, the aCSF does not comprise glucose or proteins.

Preferably the viral vector comprises a therapeutic agent, such as a transgene. Gene therapy, as is well known, is the use of genetic material to modulate or add to genes in an individual's cells in order to treat disease. The genetic material to be introduced, i.e. the transgene, may be any appropriate genetic material, including DNA, RNA, small interfering RNA (siRNA) and short hairpin RNA (shRNA). The transgene may be used to treat the disease in any known manner, such as gene replacement, gene knockdown, pro-survival gene therapy and cell suicide therapy. Preferred transgenes for use in the invention act on expression of one or more of neurotrophins, hexosaminidases, iduronate-2-sulfatase, alpha-L iduronidase, CLN2, glucocerebrosidase or amyloid-beta degrading enzymes.

Preferably the neurological disorders treated by the viral vectors involve the cerebral cortex. Such neurological disorders can include neurodegenerative diseases, enzyme deficient conditions, neuroinflammatory diseases and acquired neurological injuries.

Neurodegenerative diseases can include dementia, Alzheimer's disease, Huntington's disease, motor neuron diseases such as Amyotrophic Lateral Sclerosis (ALS), Multiple System Atrophy and Corticobasal degeneration.

Enzyme deficient conditions can include Tay Sachs Disease, Sandhoff Disease, Neuronal Ceroid Lipofuscinosis, Hunter Syndrome, Hurler disease and Gaucher's Disease.

Neuroinflammatory disease can include Multiple Sclerosis and Creutzfeldt-Jakob Disease. Acquired neurological injury can include stroke and traumatic brain injury.

The present invention additionally provides kits comprising at least one viral vector and at least one therapeutic agent. Preferably the kits are for use in the treatment of neurological disorders, more preferably the kits are for use in the treatment of neurological disorders involving the cerebral cortex.

The kits may further comprise a convection enhanced delivery (CED) catheter. In preferred embodiments of the invention the catheter has an external diameter of not more than 600 µm. Appropriate catheters are described in WO03/077785. It may also comprise a port for connecting the catheters to a delivery device. Such ports are described in WO2008/062173 and WO2011/098769.

Also provided is a dosage vessel comprising a viral vector, wherein the dosage vessel is arranged to deliver the viral vector at a concentration or flow rate or for an infusion time as described above. The dosage vessel may be for example a sealed tube that can be connected in fluid communication to a port as described.

BRIEF DESCRIPTION OF THE DRAWINGS

The invention is now described in specific embodiments with reference to accompanying drawings in which:

FIG. 1 shows representative real-time MR images with the infused volume at the time of the scan from all 6 white matter infusions demonstrating that the distribution of contrast was restricted to white matter. Infusate did not reflux beyond the gray/white matter interface in any infusion (a-f). Leakage of infusate into cortical sulci was detected in 2 infusions (g & h). In both cases, leakage began when the volume of infusion exceeded 100 μl (arrows). Analysis of post-operative MR images revealed inadvertent breach of the sulci into which infusate subsequently leaked on catheter implantation. These infusions resulted in the lowest Vd/Vi. Coronal and corresponding MR images following infusion of 700 μl via two frontally placed catheters (*) show distribution throughout the majority of frontal white matter (i & j).

FIG. 6 shows a schematic comparison of the volume of diffusion of a pharmaceutical agent or composition administered by CED, infusion or injection into the grey matter of the motor cortex (FIG. 6A); intracerebral infusion or injection into the sub-cortical white matter below the motor cortex (FIG. 6B); and CED administration into the sub-cortical white matter of the motor cortex as provided by the present invention (FIG. 6C).

EXAMPLES

Example 1

All work was conducted in accordance with the Animals (Scientific Procedures) Act (1986) and with the authority of appropriate UK Home Office project and personal licences. Study protocols were pre-approved by the University of Bristol Ethical Review Board.

NIH Minipig Anaesthesia

A total of 6 NIH miniature pigs (aged 6 months, 40-45 kg) were used in the study. Pre-anaesthetic medication comprising azaparone (2 mg/kg, Janssen Ltd., Bucks, UK) and ketamine (10 mg/kg, Vetoquinol Ltd. Buckingham, UK) were administered by deep intramuscular injection into the dorso-lateral neck muscles. Propofol (Abbot Laboratories, Kent, UK) was used for induction of anaesthesia, and anaesthesia maintained with isofluorane (Isoflo, Abbot Laboratories). Morphine 0.1 mg/kg (Morphine sulphate, Martindale Pharmaceuticals Ltd., Essex, UK) and Meloxicam 0.4 mg/kg slow IV, (Metacam 20 mg/ml solution for injection, Boehringer Ingelheim Vet Medica GmbH., Ingelheim, Germany) were administered for analgesia by intravenous injection.

Head Immobilisation and Brain Imaging

Head immobilisation and brain imaging were achieved as previously described (Bienemann et al., 2012; White et al., 2010) with minor modifications. An MRI-compatible polyurethane head frame was attached to the animal using 2 zygomatic screws, a mouldable palate tray and Velco snout strap. A fiducial arc was then placed onto the frame to facilitate pre-operative surgical planning. The animal was transferred to the MRI scanner, where Flex-L coils were attached to the fiducial arc and pre-operative scanning performed.

A Pathfinder robotic arm (Prosurgics, High Wycombe, UK) and surgical planning software (Mayfield ACCISS-II) were used for all catheter implantation procedures. Catheter entry points, targets and safe trajectories were planned in ACCISS-II. Following identification of the site(s) for catheter entry into the brain, a U-shaped scalp flap was raised and the skull surface exposed. Robot-guided hand-drills were used for drilling of precise burr-holes into which the catheter hub would push fit. The burr hole tooling comprised of a 1.2 mm drill followed by a 5 mm drill.

Catheter Design

The implantable catheter system previously used for chronic and intermittent infusions into the porcine putamen (Bienemann et al., 2012) was used for white matter infusions with minor modifications. CED catheters were supplied by Renishaw (Renishaw Plc., Wotton-under-Edge, UK). The catheter system was composed of two components:
1. A carbothane guide-tube inserted on a tungsten carbide guide rod (outer diameter of 0.7 mm and inner diameter of 0.6 mm)
2. A central catheter composed of a carbothane tube (outer diameter of 0.6 mm/inner diameter 0.4 mm) protruding a variable distance from the distal end of the guide tube.

Catheter Insertion Procedure

The 1.2 mm drill was used to penetrate the full skull thickness at the chosen catheter entry location, and also to perforate the dura. The 5 mm hand-drill was then used to form a burr hole to accommodate the guide-tube hub. The catheters were then implanted. In all pre-operative surgical plans, we aimed to place the guide-tube tip at the junction of the cortical gray matter and underlying white matter of the frontal corona radiata. The catheter tip extended between 5 and 7.5 mm from the guide-tube tip in all procedures.

The proximal end of the catheter was attached to a commercially available septum seal (SoloPort™—Instech Laboratories, USA). The septum seal was implanted subcutaneously and allowed infusions to be performed percutaneously by insertion of a needle attached to an infusion line. The wound was closed with continuous 3/0 Vicryl sutures.

On completion of CED infusions, the animal was then taken out of the head fixation device and the zygomatic wounds closed with interrupted 3/0 Vicryl sutures. The animal was then woken from general anaesthesia. When the animal was able to protect its own airway, it was extubated and allowed to recover in isolation for 24 hours. Animals were inspected twice daily during the recovery period for signs of wound infection or breakdown, neurological deficits or abnormal behaviour.

Contrast Infusions in White Matter

Infusions of 0.2% Gadolinium-DTPA (Magnevist, Bayer Healthcare, Germany) mixed in sterile artificial cerebrospinal fluid (aCSF, Torbay Pharmaceutical Manufacturing Unit, Paignton, UK) were undertaken immediately following catheter implantation using the following ramping regime—0.5 µl/min for 5 min, 1.0 µl/min for 5 min, 2.5 µl/min for 5 min, 5 µl/min for 10 min±10 µl/min until completion.

The total volume of infusion ranged from 182.5 µl to 700 µl per catheter. A total of 6 white matter infusions performed in 6 animals were used for volume of distribution analysis. In the sixth animal two catheters were also implanted into the anterior and posterior frontal white matter of the same hemisphere in order to determine whether high volume infusions might facilitate distribution of contrast throughout the whole frontal corona radiata.

Co-infusion of AAV2/5-GFP

In 3 infusions, adeno-associated virus of serotype 2/5 expressing enhanced green fluorescent protein (AAV5-GFP, Vector Biolabs, Philadelphia, USA) was co-infused with 0.2% Gadolinium-DTPA in aCSF. The construct comprised an AAV5 capsid, an AAV2 Inverted Terminal Repeat sequence and CMV promoter. Infusions were performed at a concentration of $10^{10}$ Vg/ml.

MRI Acquisition

Imaging was undertaken using an MRI scanner with field strength of 1.5 T (Intera, Philips, UK). Pre-operative MR imaging comprised contiguous T1-weighted coronal slices (0.8 mm slice thickness) of a volume which included fiducials and brain. For subsequent T1-weighted imaging (repeated at 15 minute intervals) the parameters were—FOV: AP 200 mm: RL 159 mm: FH72 mm; voxel size: AP 0.575 mm; FH 0.8 mm; matrix size: M×P 378×277. The brain was aligned on the anterior commissure-posterior commissure line (AC-PC) to facilitate comparison with histological analysis.

MM Analysis of Volume of Distribution

Volume of distribution analysis was performed on consecutive 0.8 mm thick T1-weighted MR images with a semi-automated application developed in-house using MATLAB software (MathWorks, Cambridge, UK). This application allowed the observer to identify a region of interest, and then to manually highlight the area of Gadolinium (Gd) distribution on each scan slice throughout the volume of distribution. The software then calculated the total volume from the area highlighted by the observer and the thickness of each scan slice. The software was validated by analysing fiducial spheres of known volume, and was found to be accurate to within 0.1 ml. All volumes were independently analysed by a 3 observers using standardised contrast and gain settings, and the mean volume of distribution (±SD) calculated for each infusion. Six historical infusions of 0.2% Gd-aCSF in gray matter (putamen) were analysed for comparison (Bienemann et al., 2012).

Immunohistochemical Analysis of Cell Transduction

Animals were terminated at 1 month following CED of AAV2/5-GFP following transcardial perfusion-fixation with 10% formalin. Brains were explanted and post-fixed in 10% formalin for 2 weeks, then cryprotected in 30% sucrose-formalin. Pig brains were aligned on AC-PC prior to sectioning to facilitate comparison with MR images, and cut into 100 µm coronal sections using a Leica SM2500 microtome (Leica microsystems, Milton Keynes, UK).

Fluorescence Immunohistochemistry

Sections incorporating the catheter track and at 4 mm intervals anterior and posterior to the catheter were selected for immunolabeling. Expression of GFP was co-localised with neurons, astrocytes and oligodendrocytes by immunolabeling with mouse anti-NeuN (1:300; Chemicon, UK), rabbit anti-GFAP (1:300; Chemicon) and mouse anti-CNPase (1:500; Abcam, Cambridge, UK). For fluorescence immunohistochemistry, Cy3 (Jackson Laboratories, CA, USA) species-specific secondary antibodies were used at a dilution of 1:200. All incubations with primary antibodies were for 18 hours at 4° C., and 2 hours at room temperature for secondary antibodies. Brightfield, differential interference contrast (DIC) and fluorescence imaging was performed using a Leica DM5500 microscope (Leica Microsystems).

DAB (3',3'-diaminobenzidine) Immunohistochemistry

Sections incorporating the catheter track and at 4 mm intervals anterior and posterior to the catheter were selected for DAB immunolabeling. Sections were incubated with GFP primary antibody (1:1000; Abcam) for 18 hours at 4° C., then rabbit anti-chicken HRP secondary antibody (1:300; Abcam, UK) for 1 hour at room temperature. Following three PBS washes, DAB reagent (Peroxidase Substrate Kit; Vector Laboratories, Burlingame, USA) was applied to mounted sections for 2 minutes to allow DAB colour to develop. The DAB reaction was stopped with two distilled water washes and sections were dehydrated with increasing concentrations of alcohol followed by immersion in xylene. Finally, sections were coverslipped with Perspex mounting reagent (CellPath, UK) and brightfield imaging performed using a Leica DM5500 microscope (Leica Microsystems).

RESULTS

CED in White Matter

Figure 1:
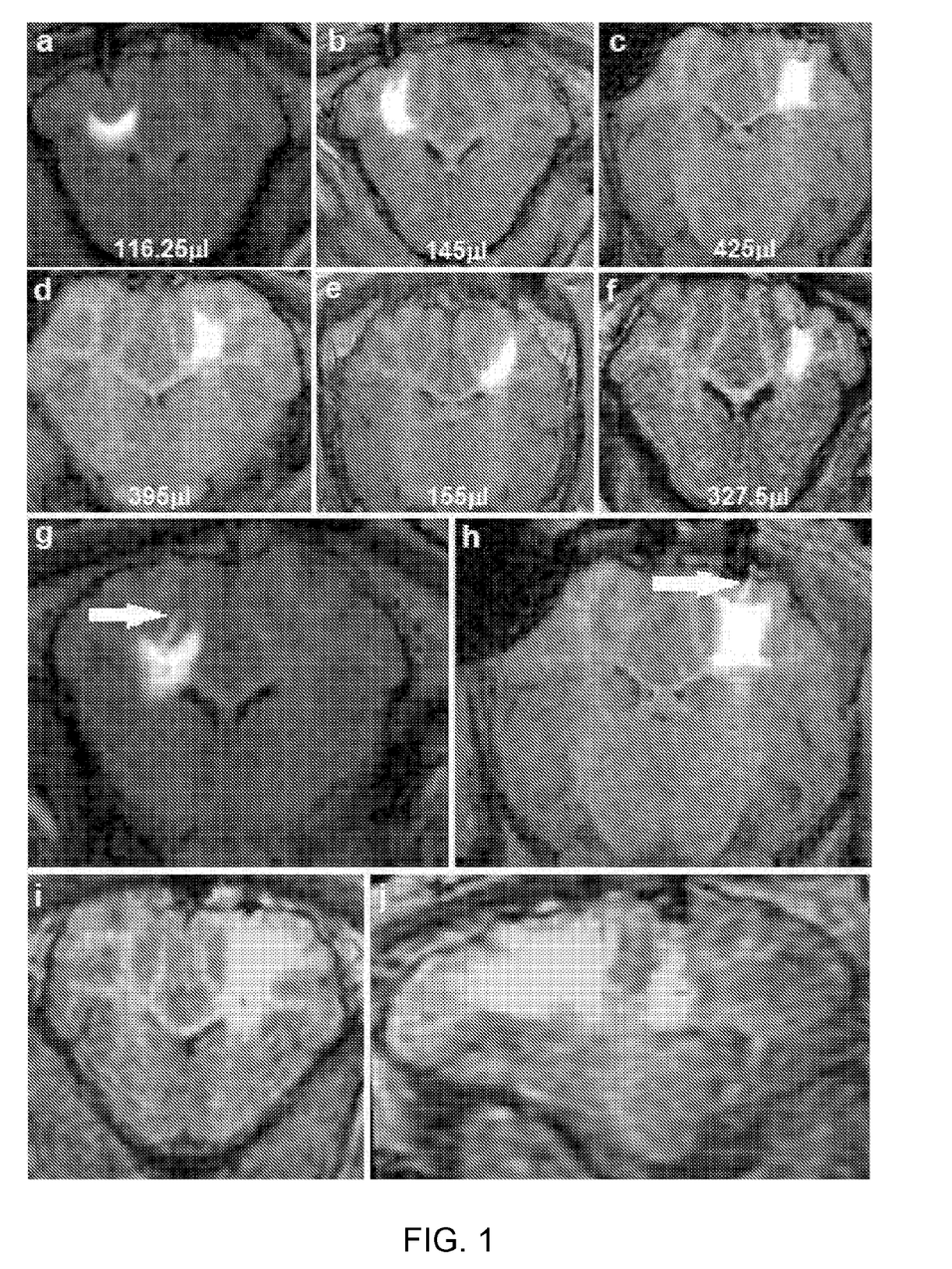

A total of 8 infusions of 0.2% Gd-aCSF were successfully performed in 6 animals immediately following catheter implantation. In all cases the guide-tube tip was placed at the junction of cortical gray matter and underlying frontal corona radiata, and the catheter tip placed between 5 and 7.5 mm beyond the guide-tube. None of the infusions of contrast were seen to reflux beyond the cortical gray-white matter interface on MRI (FIGS. 1a-f), and no animal suffered adverse neurological sequelae despite infusion of relatively high volumes at flow rates up to 10 µl/min. No leakage of contrast into the frontal horn of the lateral ventricle, or effacement of the lateral ventricle was observed in any infusion. A summary of infusions is shown in Table 1.

TABLE 1

Summary of white matter infusions

| | Volume of infusion (Vi, μl) | Volume of distribution (Vd, μl)* | Vd/Vi (mean ± SD)* | Max infusion flow rate (μl/min) | Leakage into sulcus | Co-infusion of AAV2/5-GFP |
|---|---|---|---|---|---|---|
| 1 | 116.25 | 367.2 | 3.16 ± 0.26 | 5 | No | No |
| 2 | 145 | 290.3 | 1.81 ± 0.04 | 5 | Yes | No |
| 3 | 155 | 342.9 | 2.19 ± 0.51 | 5 | Yes | No |
| 4 | 327.5 | 757.3 | 2.51 ± 0.24 | 10 | No | Yes |
| 5 | 395 | 865 | 2.21 ± 0.08 | 10 | No | Yes |
| 6 | 425 | 1048.8 | 2.47 ± 0.4 | 10 | No | Yes |

*Mean of 3 independent analyses

Leakage of Infusate into Sulci

In 2 infusions, the infusate initially distributed in white matter and then leaked into cortical sulci. In both cases, leakage into sulci began when the volume of infusion exceeded 100 μl (FIGS. 1g & h). On analysis of MR imaging obtained following catheter implantation, it was evident that the trajectory of catheter insertion had inadvertently breached the deep sulcus into which infusate subsequently leaked.

Infusion Via Two Frontal Catheters

Infusions were ramped to 10 μl/min and continued to deliver a total volume of 700 μl of 0.2% Gd-aCSF per catheter. After 90 minutes of infusion, contrast was seen to distribute throughout the majority of the frontal white matter forming a single distribution cloud (FIGS. 1i & j). It was not possible to accurately analyse Vd/Vi (ratio of volume of distribution to volume of infusion) from these two catheters due to joining of the infusate distributions. The animal recovered with no evidence of adverse neurological sequelae.

MRI Volume of Distribution Analysis

Figure 2:
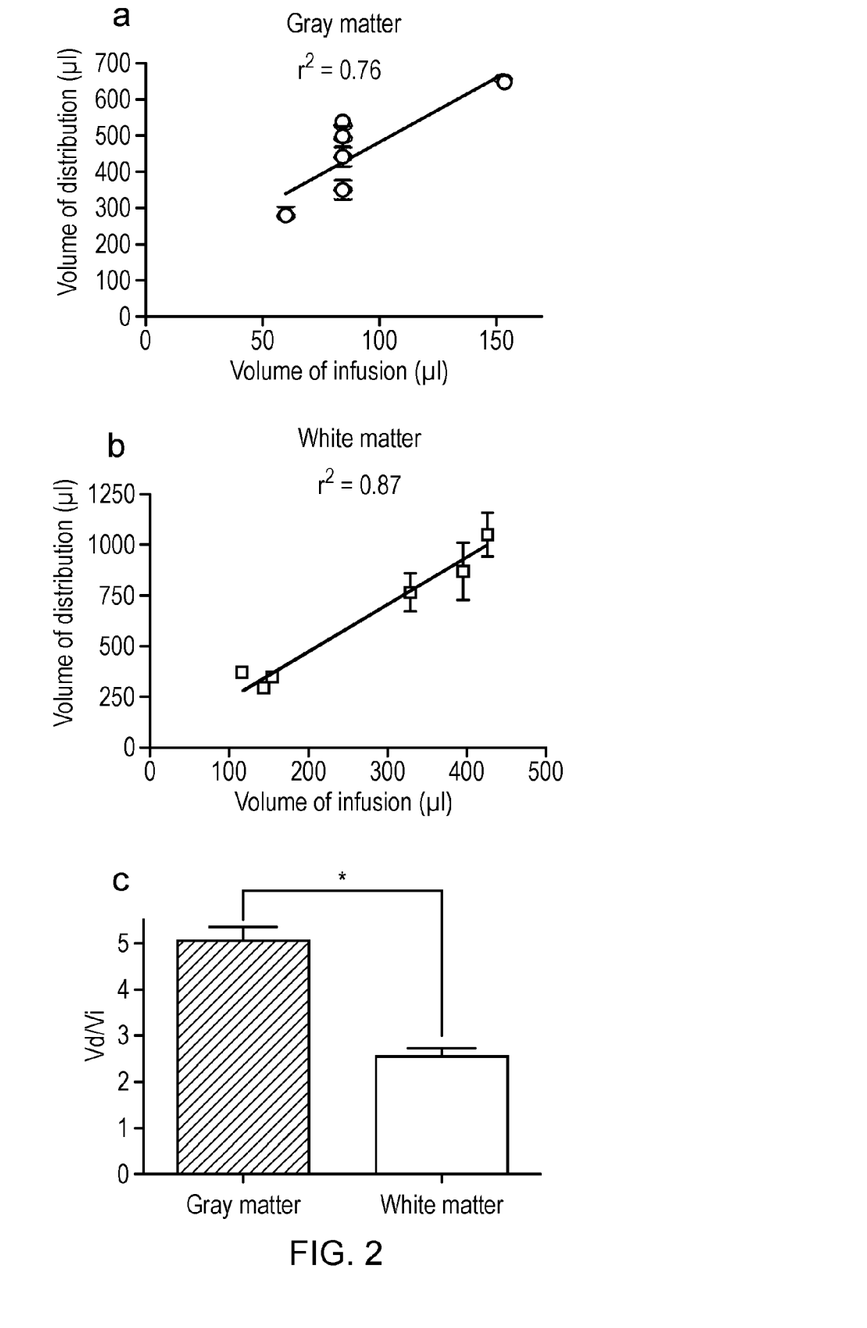
FIG. 2 shows a comparison of ratio of Vd/Vi in gray (a) and white (b) matter. Lines represent least squares regression. Comparison of mean (±SEM) ratios (c) showed significantly higher Vd/Vi in gray matter (p=0.0004).

The mean Vd/Vi (±SD) in the 6 white matter infusions suitable for volumetric analysis was 2.55±0.42 (range 1.84 to 2.96). Leakage of contrast into cortical sulci was associated with the lowest Vd/Vi—1.84 and 2.19. When infusions associated with leakage of contrast into sulci are excluded from the analysis, the Vd/Vi increased to 2.79±0.18. The Vd/Vi in 6 historical infusions performed into the putamen of NIH miniature pigs was significantly higher with a mean (±SD) of 5.06±0.7 (p=0.0004, paired t-test). Comparison of the Vd/Vi in gray and white matter is shown in FIG. 2.

Infusion of AAV2/5-GFP

Figure 3:
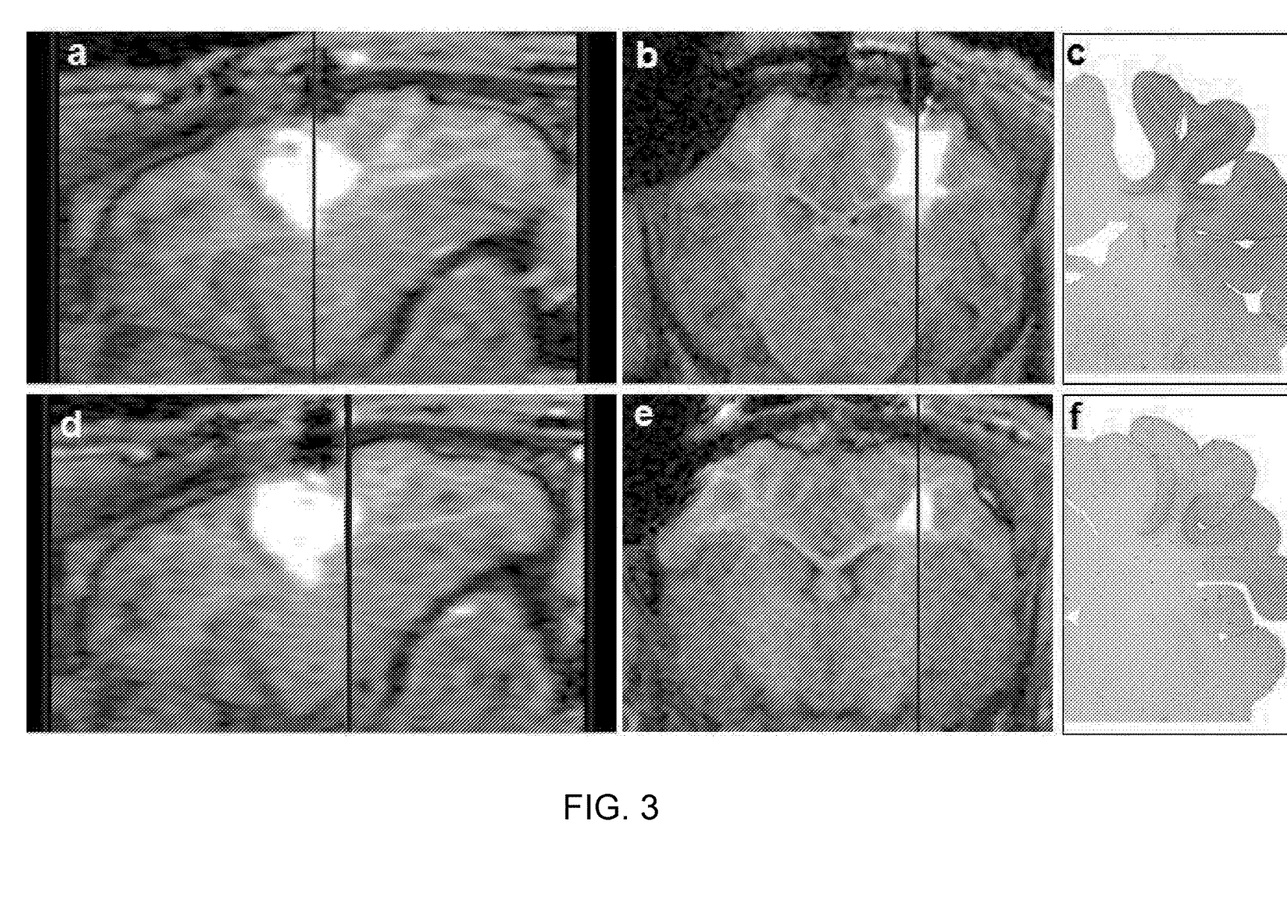
FIG. 3 shows sagittal (a & d) and corresponding coronal (b & e) MR images show distribution of 0.2% Gd-aCSF to correlate closely with GFP expression detected by DAB immunostaining (c & f) at one month post-infusion of AAV2/5-GFP. Neuronal transduction at the gray/white interface with GFP expression in more superficial cortical layers is evident in areas of cortex adjacent to contrast distribution on MRI.
Figure 4:
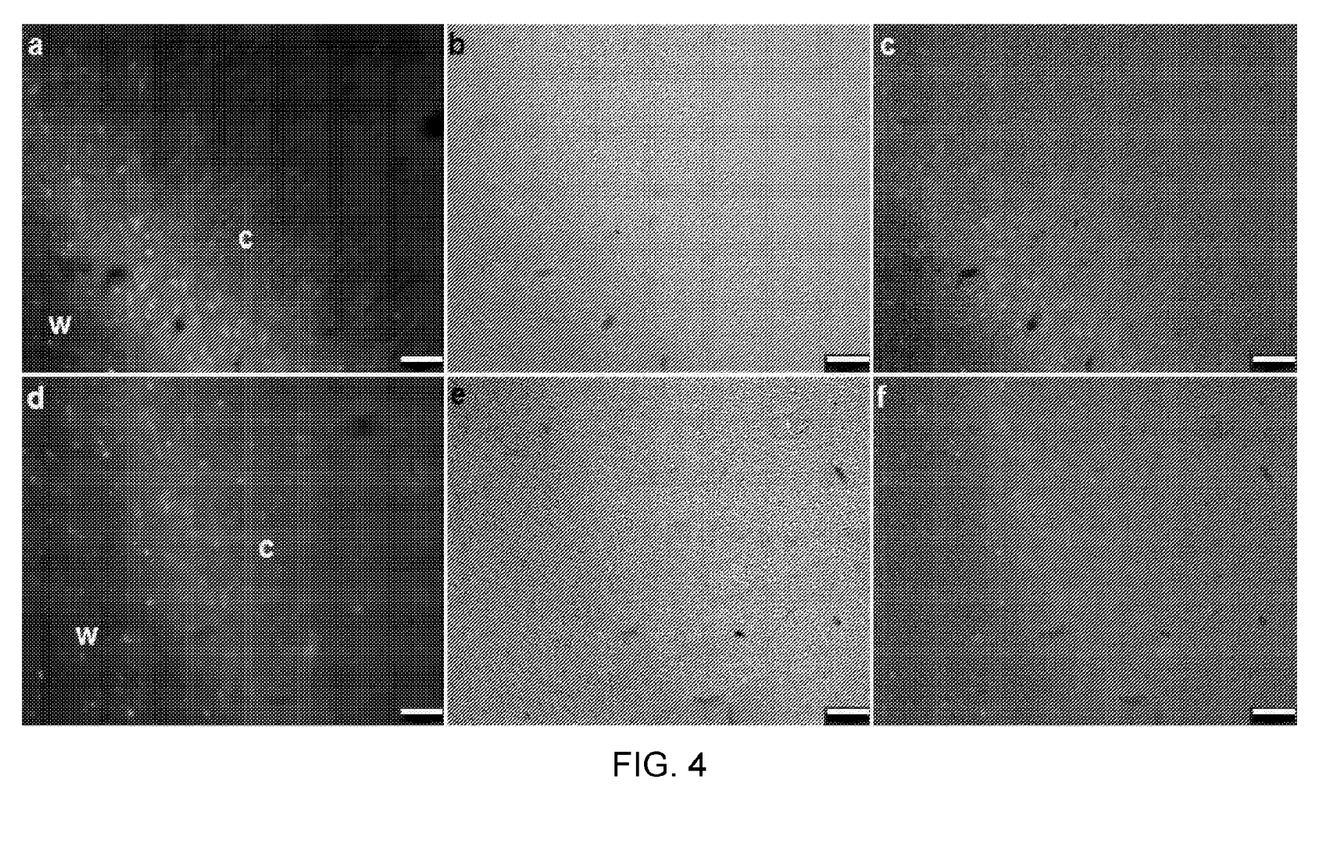
FIG. 4 shows fluorescence (a & d), DIC (b & e) and merged images (c & f) at the junction of white matter (W) and overlying cortex (C) reveals neuronal transduction at the interface with axonal transport of GFP to more superficial cortical layers. Scale bar=100 μm.

Infusion of AAV2/5-GFP resulted in widespread cortical expression of GFP at one month following CED. The histological distribution of cortical GFP expression using DAB immunohistochemistry correlated well with the distribution of contrast in underlying white matter on MRI. DAB immunohistochemistry and DIC microscopy indicated neuronal cell body transduction at the interface of the white matter with overlying cortical gray matter, with GFP expression throughout more superficial cortical layers (FIGS. 3 & 4). Only cortical regions immediately adjacent to areas of contrast distribution on MRI were seen to express GFP.

Figure 5:
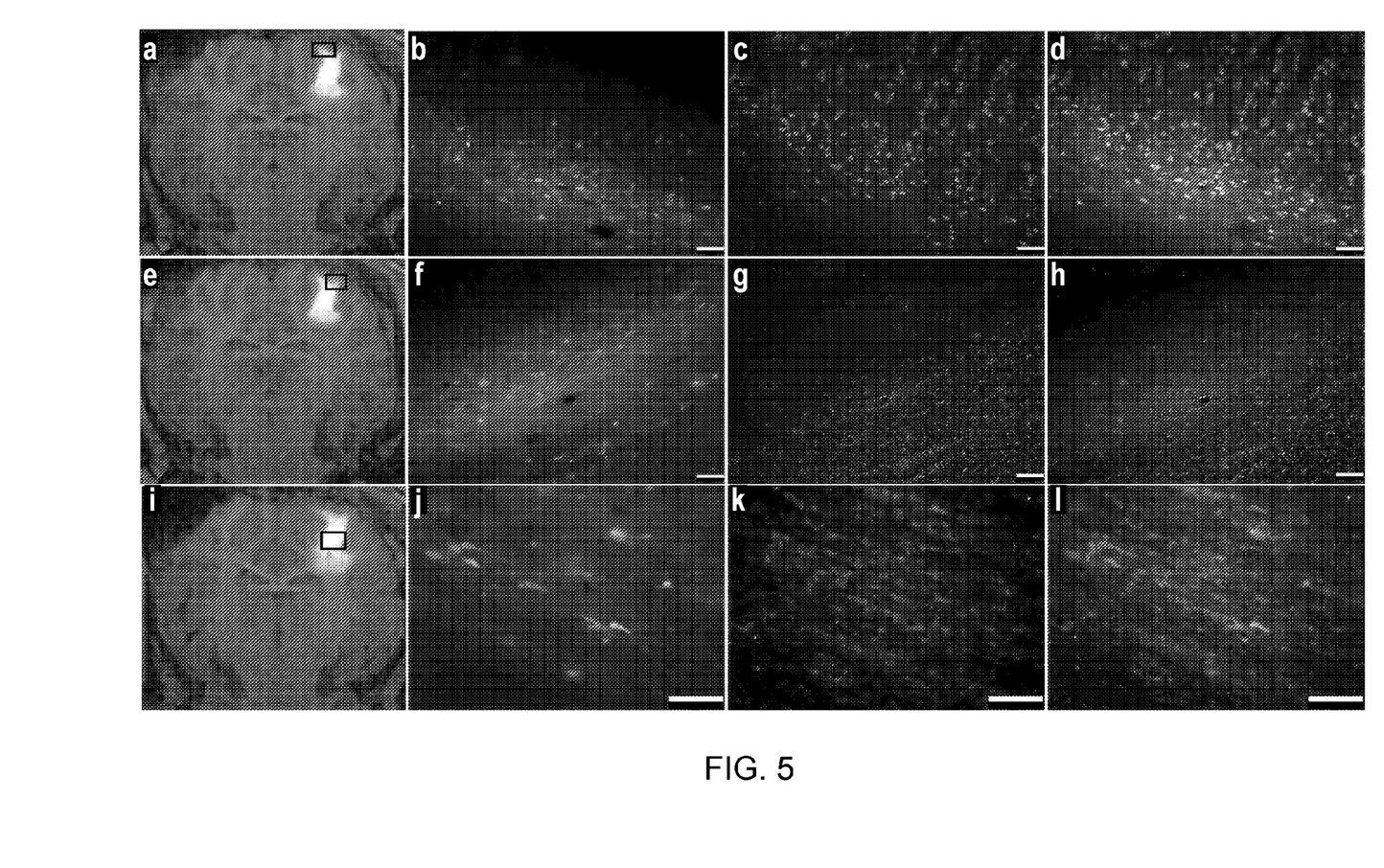
FIG. 5 shows one month following co-infusion of 0.2% Gd-aCSF and AAV2/5-GFP fluorescence immunohistochemistry demonstrates widespread neuronal transduction (NeuN, red, b-d) at the junction of white matter and cortical gray matter. There was also evidence of transduction of scattered astrocytes (GFAP, red f-h) and oligodendrocytes (CNPase, red, j-i) throughout the areas of white matter which correlated with distribution of contrast seen on Mill (a, e & i). Scale bar=100 μm.
Figure 6A:
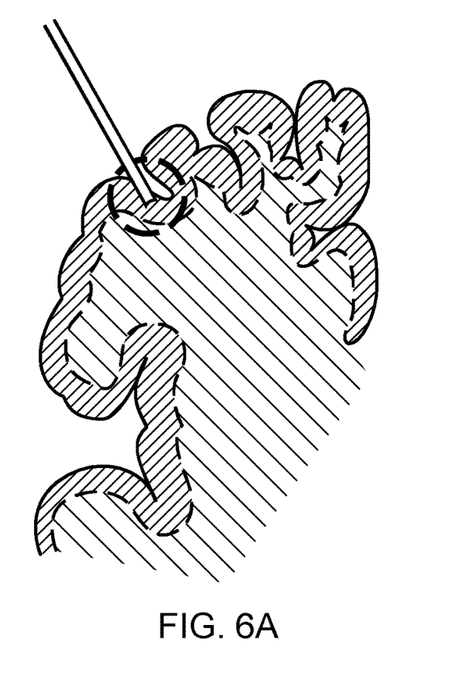
Figure 6B:
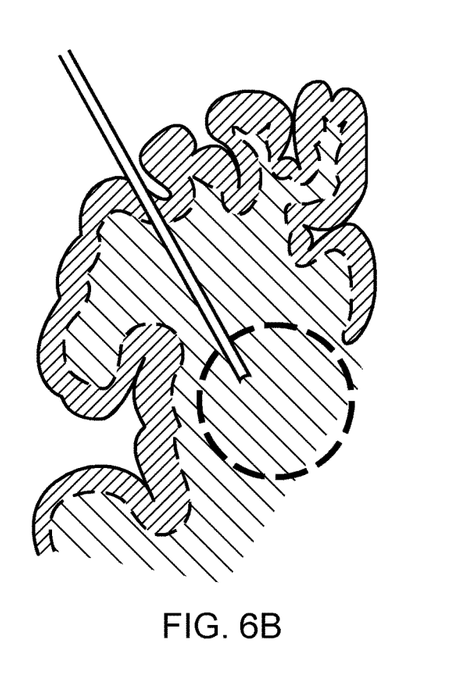
Figure 6C:
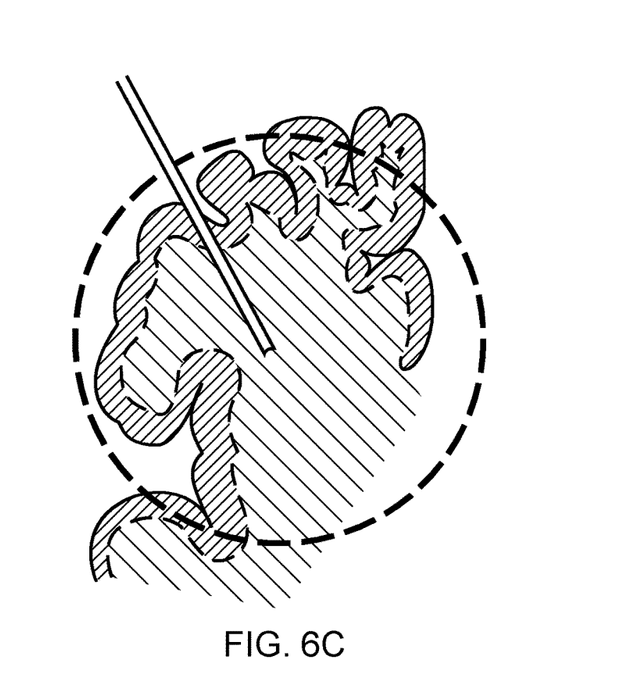

Fluorescence immunohistochemistry confirmed widespread transduction of neurons in the deep layers of cortex overlying the areas of white matter infusion, as well as transduction of occasional astrocytes and oligodendocytes throughout the corona radiata (FIG. 5).

DISCUSSION

The results of this study show high volume, high flow CED infusions in white matter without reflux of infusate beyond the gray/white matter interface.

In Bobo et al.'s original description of convection-enhanced delivery of macromolecules (Bobo et al., 1994), isotope-labelled transferrin and sucrose were infused into the corona radiata of cats. The Vd/Vi determined by quantitative autoradiography was 6 for transferrin and 13 for sucrose. Both sucrose and transferrin continued to re-distribute across the gray/white matter junction into overlying cortex on completion of white matter infusions, although sucrose was seen to re-distribute more quickly.

In the present study, infusions of 0.2% Gd-aCSF into the corona radiata of NIH miniature pigs resulted in a much lower Vd/Vi, based on MRI volumetric analysis. With a molecular weight of 0.56 kDa, Gd-DTPA might be expected to have similar distribution characteristics to sucrose (MW=0.34 kDa). However, we have found a Vd/Vi of only 2.55. Using the same method of MRI volumetric analysis for gray matter (putaminal) infusions we have found a Vd/Vi of 5, which is consistent with previous reports using both histological and MRI methods to determine distribution in the putamen of non-human primates. These data suggest that our method of volume analysis is valid, and also that quantitative autoradiography might over-estimate the distribution of isotope-labelled infusates.

The reasons for the higher Vd/Vi seen in gray matter might reflect differences in the elasticity of these two tissue types. The evidence for whether gray or white matter is more elastic is inconsistent and controversial, with some investigators assuming much greater stiffness in gray matter without adequate justification (Prange et al., 2000). In a study comparing the stiffness of thalamic gray matter with the white matter of the corona radiata of fresh pig brain, Prange et al. found gray matter to be in an average sense 30% stiffer than white matter (Prange et al., 2000).

Our findings support a higher elasticity in white matter, with high volume infusions expanding the interstitium and thus limiting the volume of distribution. Expansion of the volume fraction of the interstitium during white matter infusions has been reported with quantitative concentration measurements of MRI contrast agents. The greater anisotropy of white matter due to the orthogonal arrangement of fibre tracts might also limit the distribution of infusates delivered by CED.

An understanding of the relationship between infused volume and volume of distribution has significant implications for clinical translation. The water content of normal white and gray matter is said to be approximately 70% and 80% respectively. Consequently the relationship of the infused concentration of a drug to the tissue concentration might differ considerably between white and gray matter infusions.

Real-time MR imaging of infusions in the present study also suggested that the distribution of infusate is restricted to white matter, and does not distribute efficiently across the gray/white matter interface into overlying cortex. This observation is corroborated by histological analysis of brains infused with AAV2/5-GFP which demonstrated transduction of neurons at the gray/white matter interface, with evidence of axonal transport of GFP to superficial cortical layers.

The lowest Vd/Vi ratios were seen when infusate leaked into cortical sulci. It seems likely that the cause of leakage was inadvertent breaching of deep sulci on catheter insertion. This finding highlights the importance of high quality pre-operative imaging and meticulous trajectory planning for the translation of CED to clinical practice, as leakage of infusates into the subarachnoid spaces could have deleterious consequences for patients.

When catheter implantations did not breach cortical sulci, it was possible to achieve high volume infusions at flow rates of 10 µl/min, without reflux of infusate beyond the cortex/white matter interface and without adverse neurological sequelae. The facility to use high flow rates is of paramount importance for clinical translation of CED, to limit the time of infusions to periods which are acceptable to patients, whilst distributing therapeutic agents through clinically-relevant brain volumes. By infusing via two frontally-placed catheters, it was possible to distribute contrast throughout the majority of the frontal white matter with a relatively short infusion time. However, this study suggests that the ratio of volume of infusion to volume of distribution in white matter may be lower than previously described.

Recent clinical trials using AAV2 serotypes to deliver gene therapies have confirmed the safety and efficacy of this vector, and AAV2 is emerging as the preferred vehicle for gene-based treatment of neurological disorders. In the present study co-infusion of AAV2/5-GFP and 0.2% Gd-aCSF into white matter resulted in transduction of neurons at the gray/white matter interface adjacent to areas of contrast distribution on MRI, with expression of GFP in more superficial cortical layers. The areas of cortical GFP expression correlated well with the distribution of contrast seen on MM.

This novel method of targeting viral vector-mediated gene therapies to cerebral cortex might have a number of advantages over the previously described method of targeting gene-therapies to the cerebral cortex, which exploits retro- and antero-grade axonal trafficking from the thalamus. In order to target specific areas of cortex, individual thalamic nuclei would have to be targeted—something which may not be practicable in a clinical setting because specific thalamic nuclei are not easily visualized with conventional imaging methods. Historically, reflux and poor drug distribution have been problematic when targeting subcortical gray matter structures which could increase the risk of adverse effects from intrathalamic CED.

In the present study we have been able to target AAV2/5-GFP to specific areas of cortex by performing CED into underlying white matter. This novel method of gene delivery could have application to a range of neurological disorders which are characterised by atrophy of specific areas of cortex such as amyotrophic lateral sclerosis (motor cortex) and Alzheimer's Disease (parietal and entorhinal cortex). Further studies are required to determine whether CED of gene therapies into white matter might ameliorate cortical dysfunction in such diseases.

REFERENCES

Bienemann A, White E, Woolley M, Castrique E, Johnson D E, Wyatt M, Murray G, Taylor H, Barua N, Gill S S. The development of an implantable catheter system for chronic or intermittent convection-enhanced delivery. Journal of neuroscience methods, 2012; 203:284-91.

Bobo R H, Laske D W, Akbasak A, Morrison P F, Dedrick R L, Oldfield E H. Convection-enhanced delivery of macromolecules in the brain. Proc Natl Acad Sci USA, 1994; 91:2076-80.

Prange M T, Meaney D F, Margulies S S. Defining brain mechanical properties: effects of region, direction, and species. Stapp Car Crash J, 2000; 44:205-13.

White E, Woolley M, Bienemann A, Johnson D E, Wyatt M, Murray G, Taylor H, Gill S S. A robust MRI-compatible system to facilitate highly accurate stereotactic administration of therapeutic agents to targets within the brain of a large animal model. Journal of neuroscience methods, 2011; 195:78-87.

The invention claimed is:

1. A method for delivering a therapeutic transgene to a cerebral cortex or to the cerebral cortex and spinal cord, comprising administering a viral vector that comprises the therapeutic transgene into white matter of a brain in order to deliver the therapeutic transgene to the cerebral cortex or to the cerebral cortex and spinal cord,
wherein the viral vector is administered by convection enhanced diffusion (CED) below a motor cortex, visual cortex, or auditory cortex at a junction of cortical gray matter and underlying white matter.

2. The method according to claim 1, wherein the viral vector is selected from the group consisting of all serotypes of Adeno Associated Virus (AAV), AAV hybrid, Herpes simplex virus, Baculovirus, Rabies Virus, and Human Immunodeficiency Virus (HIV) viral vectors.

3. The method according to claim 1, wherein the viral vector is AAV2/5.

4. The method according to claim 1, wherein the method is performed to treat a neurological disorder selected from the group consisting of neurodegenerative diseases, enzyme deficient conditions, neuroinflammatory diseases, and acquired neurological injuries.

5. The method according to claim 1, wherein the method is performed to treat a neurodegenerative disease selected from the group consisting of dementia, Alzheimer's disease, Huntington's disease, Amyotrophic Lateral Sclerosis (ALS), Multiple System Atrophy, and Corticobasal degeneration.

6. The method according to claim 1, wherein the method is performed to treat an enzyme deficient condition selected from the group consisting of Tay Sachs Disease, Sandhoff Disease, Neuronal Ceroid Lipofuscinosis, Hunter Syndrome, Hurler disease, and Gaucher's Disease.

7. The method according to claim 1, wherein the method is performed to treat Multiple Sclerosis or Creutzfeldt-Jakob Disease.

8. The method according to claim 1, wherein the method is performed to treat a stroke or traumatic brain injury.

9. The method according to claim 1, wherein the viral vector is administered at a concentration of from $10^5$ to $10^{15}$ Vg/ml.

10. The method according to claim 1, wherein the viral vector is administered at a concentration of about $10^{10}$ Vg/ml.

11. The method according to claim 1, wherein the therapeutic transgene acts on expression of one or more of a neurotrophin, hexosaminidase, iduronate-2-sulfatase, alpha-L-iduronidase, CLN2, glucocerebrosidase, or amyloid-beta degrading enzyme.

12. The method according to claim 1, wherein the therapeutic transgene is delivered to the cerebral cortex and spinal cord of a patient.

13. The method according to claim 12, wherein the therapeutic transgene is delivered to anterior horn cells of the spinal cord.

14. The method according to claim 12, wherein the therapeutic transgene is delivered to posterior horn cells of the spinal cord.

\* \* \* \* \*